United States Patent
Deng (12)

(10) Patent No.: US 6,347,251 B1
(45) Date of Patent: Feb. 12, 2002

(54) APPARATUS AND METHOD FOR MICROWAVE HYPERTHERMIA AND ACUPUNCTURE

(76) Inventor: Tianquan Deng, BLK 218 Jurong East ST21, #08-575, Singapore 600218 (SG)

( * ) Notice: Subject to any disclaimer, the term of this patent is extended or adjusted under 35 U.S.C. 154(b) by 0 days.

(21) Appl. No.: 09/471,859

(22) Filed: Dec. 23, 1999

(51) Int. Cl.[7] ............................. A61F 2/00; A61B 18/18
(52) U.S. Cl. ......................... 607/101; 607/102; 606/41
(58) Field of Search ............................. 607/96, 98, 99, 607/101, 102, 115, 116; 606/41, 42, 45–50

(56) References Cited

U.S. PATENT DOCUMENTS

| | | | |
|---|---|---|---|
| 4,204,549 A | * | 5/1980 | Paglione |
| 4,448,198 A | | 5/1984 | Turner |
| 4,586,516 A | | 5/1986 | Turner |
| 4,621,642 A | | 11/1986 | Chen |
| 4,712,559 A | | 12/1987 | Turner |
| 4,805,616 A | * | 2/1989 | Pao |
| 5,536,267 A | | 7/1996 | Edwards et al. |
| 5,620,481 A | | 4/1997 | Desai et al. |
| 5,855,576 A | | 1/1999 | LeVeen et al. |
| 5,863,290 A | | 1/1999 | Gough et al. |
| 5,944,749 A | | 8/1999 | Fenn |
| 5,951,547 A | | 9/1999 | Gough et al. |
| 5,957,862 A | * | 9/1999 | Lu et al. ..................... 600/548 |

OTHER PUBLICATIONS

Paglione, Robert W., et al., *Microwave Applicators for Localized Hyperthermia Treatment of Malignant Tumors*, pp. 351–354.

\* cited by examiner

*Primary Examiner*—Roy Gibson
(74) *Attorney, Agent, or Firm*—Brown & Michaels, PC

(57) ABSTRACT

A microwave or other radio frequency (RF) hyperthermia system and method with improved uniformity and selection of heating. The novel apparatus has a single applicator or an array of applicators excited by the RF/microwave sources and connecting with some kind of controlling and monitoring subsystems. It is used for ether hyperthermia or acupuncture to provide invasive and noninvasive medical treatment to the target inside a human body. The individual applicator consists of a central signal coaxial needle surrounded by a plurality of secondary needles to enclose the heated target. The applicator guides the wave to move forwardly further resulting in a penetration improvement, and also to reduce the backward reflection from the radiator end, thus to make the boundary of heating pattern clear-defined. Such a guided-wave acupuncture needles or like-needles array producing a quasi-TEM electromagnetic (EM) radiation makes even one individual radiation applicator have a capability of EM energy focus. The central part of the applicator forms a coaxial cable type antenna. It also has a tunable feature to vary the position of each needle and the resonance length of the coaxial needle radiator to make individual applicator create a variable thermal pattern. In addition, the frequency, amplitude, and relative phase from each applicator of the formed array system can be varied by the RF/microwave generator, amplifier, and phase shifter to create optimized heating patterns via the feedback of a real time temperature profile and image display through a computer control. Through the hollow needles it can provide three-dimensional infusion of therapeutic materials and three-dimensional temperature measurement.

47 Claims, 5 Drawing Sheets

APPARATUS AND METHOD FOR MICROWAVE HYPERTHERMIA AND ACUPUNCTURE

BACKGROUND OF THE INVENTION

The present invention relates generally to apparatus and methods for irradiating targets with radio-frequency (RF) or microwave radiation, and more specially to systems for controlled application of radiation to biological tissues.

Although the conventional treatment such as surgery, x-ray radiation, and chemotherapy have been successful in treating cancers, they are frequently ineffective against many types of cancers and often have severe adverse side effects at the necessary treatment levels. In contrast, RF/microwave hyperthermia appears to have the potential for being extremely effective in the treatment of many or most types of human cancers without the above mentioned side effects.

It is reported that RF/microwave hyperthermia, both alone and in combination with other treatment methods, provides evidence of effectiveness. Medical researches further show that most types of human cancers can be thermally destroyed with heating up to the temperature range of 42° C.~45° C. Moreover, many types of cancerous tissues have been reported to have substantially poorer than normal heat transfer or dissipation characteristics due to reduced blood flow and decreased nutrition. Consequently, such types of cancers appear capable of preferential hyperthermia treatment.

Another well-known advantage of RF/microwave hyperthermia is that the RF/microwave energy may be controlled to form a focussed energy pattern inside the tumor tissues by controlling the power level and phase of each applicator, as well as by the arrangement of the applicator array. Thus it is possible to create a selected heating to kill cancers rather than damaging the normal cells through the above-described double selection feature of RF/microwave hyperthermia.

In the past years, various RF/microwave hyperthermia systems have been proposed, which are suitable for either invasive or noninvasive therapy, either for sub-surface tissue or a deep region, either small or large tumors. Among these systems, the radiation applicator is the key component, which may have variants such as monopole, dipole, needle-type, two-plates, waveguide end, horn, planar patch etc. Different applicators have their own preference for different hyperthermia system and suitable for different location of therapy, mainly because of the different penetration capability.

A powerful hyperthermia system should have the following basic criteria:
  The penetration depth is large enough to make the deep target be heated effectively, meanwhile not to damage the bypass and surrounding normal tissues.
  Temperature distribution within the tumor volume should be well defined and uniform, while the fall-off of temperature beyond the tumor volume should be steep.
  The focusing energy pattern can be tunable with a good resolution in order to treat different location and to vary the heating pattern for avoiding hot spots occurrence.
  A good trade-off between penetration and selection should be achieved.
  A good trade-off between uniformity and selection should be achieved.
  In addition, the level of hyperthermia should be precisely controllable, which may be through the feedback of accurate temperature and physiological monitoring.
  It is better to combine with other treatment methods in order to improve overall therapy effectiveness.

To review the existing hyperthermia devices, it is noted that most of them have not satisfied the above requirements completely, or need some improvement.

Noninvasive RF/microwave hyperthermia system employs the phase-amplitude controlled external RF/microwave radiation array, which is suitable for heating large deep target. But it suffers from the limited depth of penetration, the development of standing waves to create hot spots, and poor resolution not to make it really shift the energy peak. These shortcomings limit their applications to the small deep tumors, which most often face in practical clinical cases.

On the other hand, most existing invasive devices with a single applicator lack beam steering and uniformity of electromagnetic (EM) field.

Overall difficulties include that both invasive and noninvasive hyperthermia treatment systems have not integrated as a single device which can make the therapy more flexible and much easier to adjust the heating pattern for different depth of targets. Furthermore, even among other proposed invasive array focusing systems, the boundary of heating pattern by existing hyperthermia devices are not well defined, thus it does not realize a truly selected hyperthermia.

One typical example of noninvasive hyperthermia is Turner's invention, U.S. Pat. No. 4,586,516, in which all the dipole applicators are placed outside of the patient body thus its application is suitable for the deep large volume of tumors. For an example of invasive hyperthermia, in U.S. Pat. No. 4,448,198, after inserting into the body by aid of a medical catheter, every coaxial monopole antenna acts as radiating applicator to obtain coherent overlap of RF/microwave energy, and only allow parallel applicators in one direction in order to achieve Some other invasive devices such as U.S. Pat. No. 5,536,267, 5,855,576, and 5,951,547 employ multiple deflected needle-type electrodes to induce high frequency current through the ablation volume. These divergently deflected arrays of electrodes are used mainly for increasing radiation area. However they still lack well-defined radiation and thermal boundary.

For the microwave acupuncture application of U.S. Pat. No. 4,621,642, Chen's invention utilizes a solid or grand horn for shielding radiation back into the environment and improving the impedance matching between body and antenna. But it can not be inserted into body hence not to make microwave radiation inside the body be bounded.

Typically, the RF/microwave hyperthermia utilizes frequency band from 100 MHz to 3000 MHz. Hence significant amounts of RF/microwave energy are absorbed by surface or epidermis layers because of their high loss properties. The amount or the depth of penetration, which causes effective heating, is dependent upon the frequency of radiation. For example, the depth of penetration in the human muscle is only 3 cm at 915 MHz; while at 100 MHz, still only around 6.5 cm of penetration. It means that it is not a good way to radiate RF/microwaves from the exterior of the body to approach the deep tissues. So it is better to use, for example, a small coaxial cable antenna to deliver RF/microwave energy directly to the target that it needs to heat in the deepest location. Such a direct energy delivery scheme is very suitable for treating small deepest tumors, which is the most common case in the realistic clinical applications.

However, it is obvious that the frequency also determines the size of the radiation volume. The lower frequency is chosen, the larger size of the radiation volume must be produced, and vice versa.

In order to improve focus capability, the frequency should be chosen higher, but may cause not to heat effectively along the edge areas of the target tumor tissues because of the rapid power attenuation from the central of the inserted antenna. It means a good heating uniformity within the target is not achievable. When the frequency is set too low, the RF/microwaves may propagate or scatter into the surrounded normal tissues. This means the selection of heating is not acceptable.

The trade-off between good uniformity and good selection of heating must determine an optimized frequency of exact value. In an actual application, this is very difficult job, because the human body is such a complicated EM media, and may vary with case by case. However, lowering down the operating frequency should enlarge the radiation volume thus improve the heating uniformity inside the tumor volume; while as in the present invention, introducing a set of grounded needles locating along the tumor boundary to protect the surrounded normal tissues from radiation can improve the heating selection.

Therefore, one of the main objectives for this invention is to develop an RF/microwave hyperthermia apparatus having the basic advantages of the existing devices in the art and improving their performances and functionality.

SUMMARY OF THE INVENTION

According to the present invention, a novel apparatus comprises of a single applicator or an array of applicators excited by the RF/microwave sources and connecting with some kind of controlling and monitoring subsystems. It is used for either hyperthermia or acupuncture to provide invasive and noninvasive medical treatment to the target inside a human body.

The individual applicator consists of a central signal coaxial needle surrounded by a plurality of grounded needles to enclose the heated target. The advantages of such a configuration of the applicator are to guide the wave to move forwardly further resulting in a penetration improvement, and also to reduce the backward reflection from the radiator end, thus to make the boundary of heating pattern clear-defined.

Such a guided-wave needles array producing a quasi-TEM electromagnetic radiation makes even one individual radiation applicator have a capability of EM energy focus. The central part of the applicator forms a coaxial cable type antenna to deliver RF/microwave energy directly into the target site. It also has a tunable feature to vary the position of each needle and the resonance length of the coaxial needle radiator to make individual applicator create a variable thermal pattern.

In addition, the frequency, amplitude, and relative phase from each applicator of the formed array system can be varied by the RF/microwave generator, amplifier, and phase shifter to create optimized heating patterns via the feedback of a real time temperature profile and image display through a computer control.

The grounded needles are preferably hollow, not limited to solid. This presents two advantages, at least: one is to make it have ability to introduce a variety of therapeutic infusion mediums through the hollow grounded needles and the central hollow coaxial cable; on the other hand, make it easy to mount some temperature sensors inside the hollow. Thus it can provide three-dimensional infusion and three-dimensional temperature measurement.

Several different combination of applicator arrays or individual are suitable for use with the system to provide effective treatment to different location of the tumors or any other diseased tissues, for example, subsurface or deep, small or large, central or eccentric hyperthermia regions or acupuncture points. The invented system has integrated invasive and noninvasive hyperthermia to cancers, and invasive and noninvasive acupuncture to acupuncture points as a single device, which performs flexible and multiple functions.

The main advantages and unique features of the present invention compared with the existing devices are: using grounded needles and inserting into the body to bound or shield energy and to well define the heating boundary thus to protect the surrounded normal tissues from radiation and heating, and tuning both the radiator length and the insertion depth of the inner coaxial-cable antenna and the grounded needles to make it adjustable for different size and different depth of target tumor tissues hence varying the thermal patterns, therefore realizing a really selected and localized heating therapy.

Further scope of applicability of the present invention will become apparent from the detailed description given hereinafter. However, it should be understood that the detailed description and specific examples, while indicating preferred embodiments of the invention, are presented by way of illustration only, since various changes and modifications within the spirit and scope of the invention will become apparent to those skilled in the art from this detailed description.

BRIEF DESCRIPTION OF THE DRAWINGS

FIG. 3(a) shows a completely invasive treatment for a deepest target; FIG. 3(b) shows a partially invasive treatment for an intermediate depth target; and FIG. 3(c) shows a noninvasive treatment for a subsurface or surface target.

DESCRIPTION OF THE PREFERRED EMBODIMENTS

Figure 1:
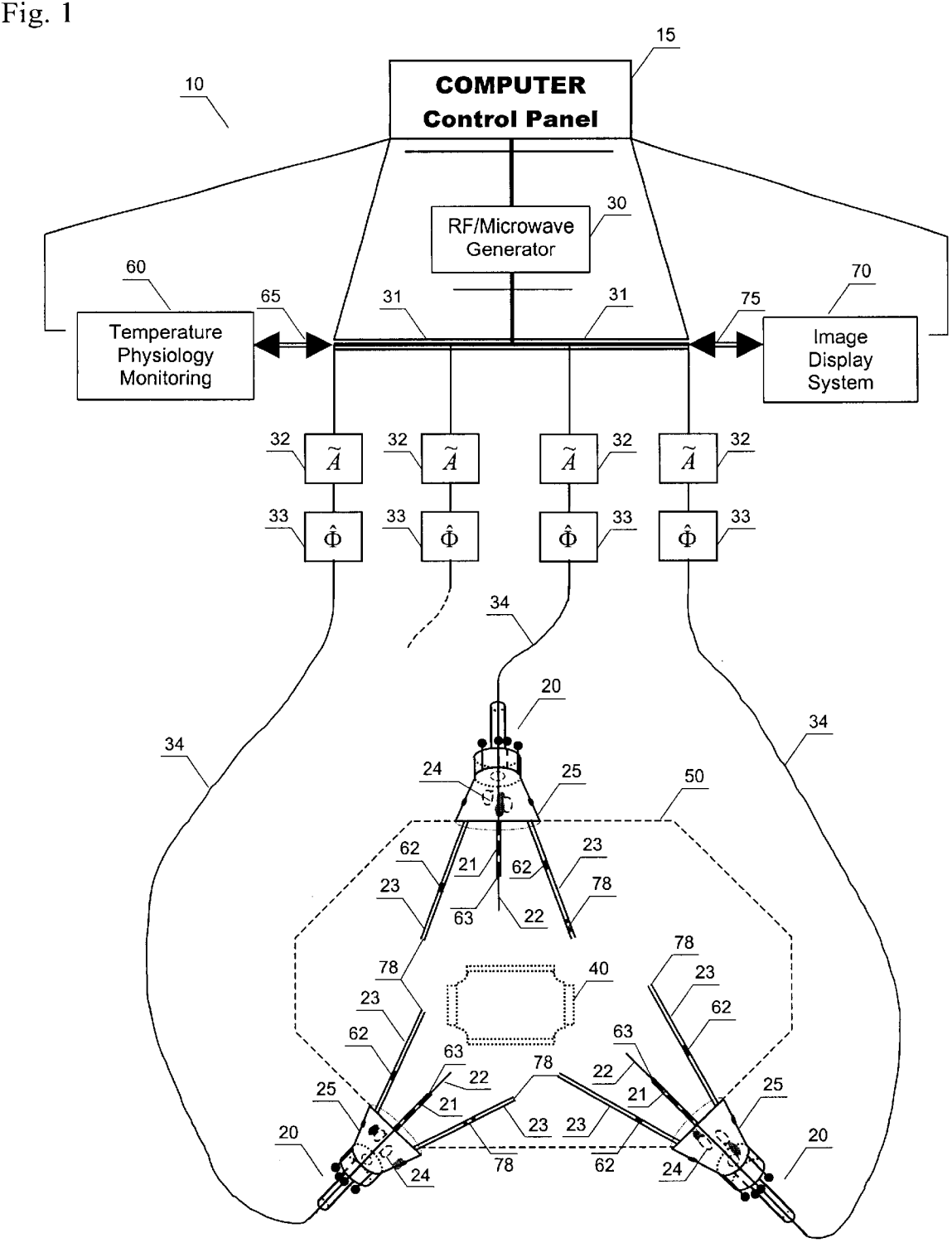
FIG. 1 is a schematic diagram of a system for the hyperthermia or acupuncture treatment to a target.

FIG. 1 shows a block diagram of a system 10 for the hyperthermia treatment in a target 40 irradiated by a single applicator or array of applicators 20. The central computer controller 15 controls and monitors the whole system 10, and is in interactive link with each of the elements. The controller 15 provides an interactive interface to accept some necessary commands and input data, for example, frequency, amplitude and phase of each applicator 20 by controlling RF/microwave power generator 30, amplifier 32, and phase shifter 33 etc.

The central computer 15 monitors the real time information about the temperature distribution inside the target 40 and the overall status of physiological signs through a temperature and physiological monitoring subsystem 60, and also displays the three-dimensional image of the location of target 40 and the inserting positions of applicators 20 through an image display subsystem 70. The information obtained provides a feedback to the central computer controller 15 to tune the system data to create an optimized heating pattern.

The RF/microwave generator 30 may be of a solid-state circuit type, or vacuum tube type, to provide a radio frequency or microwave signal at a single frequency or preferably sweep of frequencies. Due to the demand for different location and depth of targets, an RF/microwave signal with a wide range frequency of 100 MHz to 3000 MHz at power level of several tens to several hundred watts is preferred. This signal will be referred to herein as "RF/microwave", corresponding with the common use of the term in the medical field, although it will be understood by one skilled in the art that the frequencies to be applied may be outside the range which is strictly considered the "microwave" spectrum in the radio signal art.

The operation frequency should be selected properly, according to penetration depth and target size. In order to obtain effectively heating and relatively well-defined heating boundary, the half wavelength of tissue is selected to equal to or larger than the target diameter. For example, for high water content tissues such as muscle or tumor, the wavelengths at frequencies of 150, 433, 915, and 2450 MHz are approximately 18, 8.8, 4.5, and 1.8 cm respectively. The preferred way to choose the operation frequency and the power level is through the feedback of a real time measured thermal pattern to create the desired therapy, as described in detail hereinafter.

The RF/microwave generator 30 is connected to the power splitter 31. After RF/microwave signal is split into several separate channels, the amplifier 32 and phase shifter 33 may control the amplitude and phase of each channel signal respectively. Preferably, the RF/microwave generator 30, each of amplifier 32 and phase shifter 33 may have communication interfaces such as GBIP card with connection to the central computer controller 15 to automatically control their input data. The conventional RF/microwave cable 34 may be used to connect between the RF/microwave devices, also including connection of each applicator 20. Thus the final amplitude and phase of each applicator 20 can be controlled directly from the central computer controller 15. To provide the efficient impedance coupling throughout the system, all the transmission cable and input/output ports of other RF/microwave devices, as well as the feed line of each applicator and connector should be designed or commercially available equipment having characteristic impedance of 50 ohms.

Figure 2:
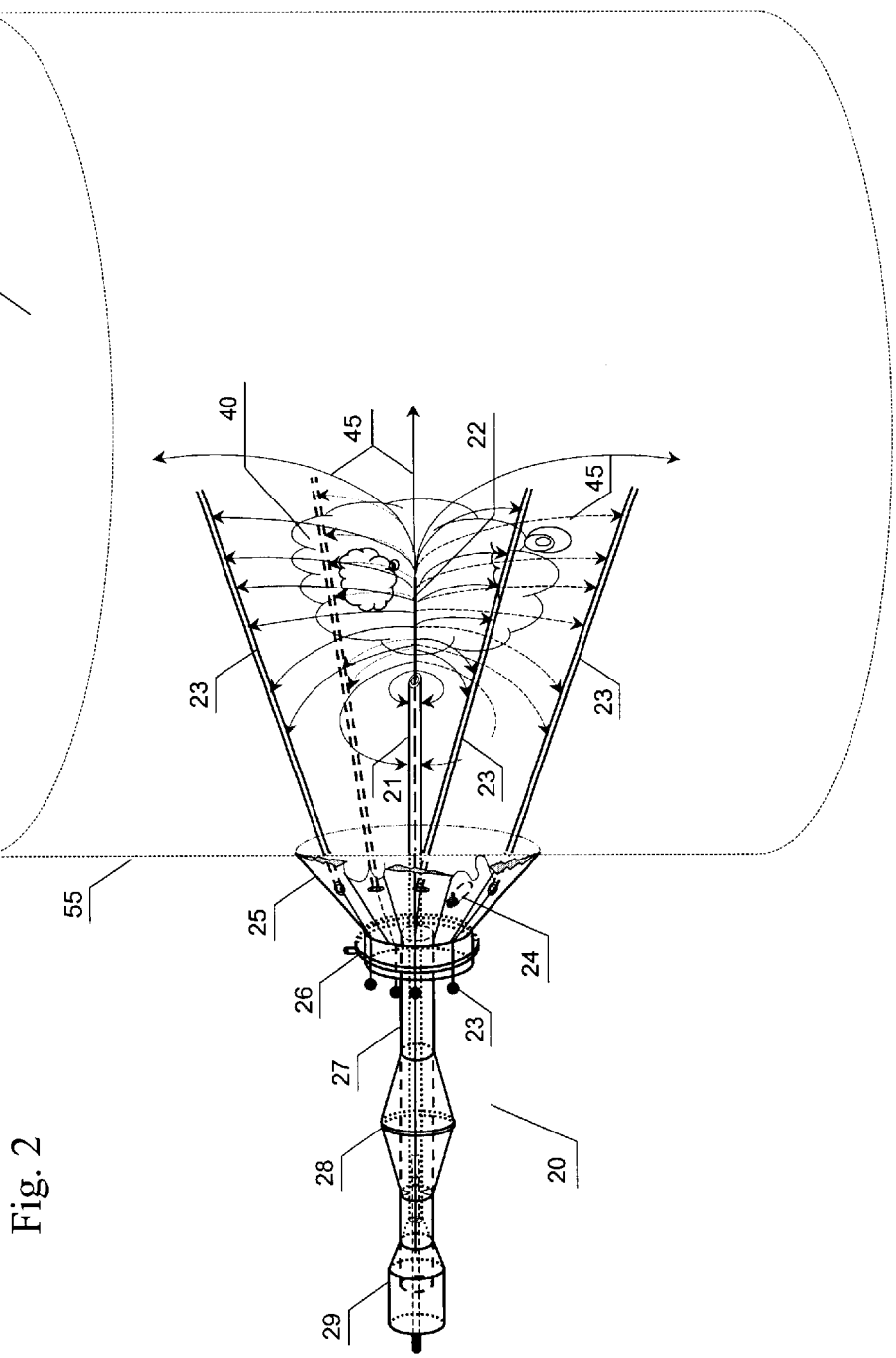
FIG. 2 is the configuration of a single applicator used in the system of FIG. 1 and showing the bounded field distribution.

Referring to both FIG. 1 and FIG. 2, the applicator 20 consists of a coaxial needle (21 plus 22) surrounded by a plurality of grounded secondary needles 23 to enclose the heated target. This thin needle may adapt a traditional Chinese acupuncture needle, but not limited to, or the like. Further, it is traditionally made of silver, but here not limited to, or any other metal having good conductivity suiting for RF/microwave transmission. For insertion purposes, silver is the best in terms of hardness and health to human tissues, and is also easily made by borrowing the technology of manufacturing traditional Chinese acupuncture needles. The needles 21, 22, 23 may be coated with, or have deposited upon them, insulation materials such as polytetrafluoroethylene (PTFE), better known as Teflon® (a trademark of the E.I DuPont de Nemours Company), or diamond to avoid direct contact with the body tissues, thereby decreasing leakage current at low frequency, and also to increase its hardness.

The central solid needle 22 is inserted into a typical hypodermic hollow stainless needle 21, or the like, while more insulation materials may be added, in-between, to isolate them and also to match to 50 Ohm characteristic impedance. A precise design and fabrication should be made so that the central solid needle 22 can be movable along the axis of the hollow outer needle 21 and let the central solid needle 22 expose a changeable radiation portion. It means that the central part of the applicator forms a coaxial cable type antenna.

The surrounding secondary needles 23 are grounded to the shielding horn 25 to form the bounded EM fields 45. After insertion through holes of the horn 25, the secondary needles 23 are fixed by the fixture 26. The said shielding horn 25 is constructed of some pieces of folded metal plates sewing together with some commercially available RF/microwave-shielding cloth. Such a soft horn is very flexible to use at different locations with various body shapes of the patient, and can easily be fixed to the body using some string or belt. Some deionized water boluses 24 are placed inside the horns thus cooling down the body surface and also improving the impedance matching to the body especially when the noninvasive applicator is operated. After that, the applicator 20 is attached with two kinds of tuners 28, 29 to respectively make the length of radiation portion and position of the coaxial cable type antenna (21 plus 22) be tunable. Any other mechanical tuning can be used, not limited to the demonstration here. The supporter 27 acts as not only the tuner sliding but also the ground connection among the outer needle 21, horn 25, tuners 28, 29, and outer conductor of the connector. Finally a standard RF/microwave connector (not shown) is employed to adapt the applicator 20 to the commercially available coaxial cable 34 which connects applicator 20 to the RF/microwave energy supply devices 30, 31, 32, 33.

The grounded secondary needles are preferably hollow, not limited to solid. Two advantages at least may have: one is to make it have ability to introduce a variety of infusion mediums through the hollow secondary needles and the central hollow coaxial cable; on the other hand, make it easy to mount some temperature sensors inside the hollow. Suitable infusion mediums may include, but not limited to, therapeutic agents, conductivity enhancement solutions, or contrast agents, and the like. In practice, some small holes 78 and the end 78 of secondary needles as well as the end 63 of the central coaxial cable are open for infusion of proper therapeutic agents. This configuration of array needles can produce a three-dimensional infusion to enclose the target tumors and subsequently to improve the infusion uniformity. Thus it combines with RF/microwave hyperthermia to greatly improve therapy effectiveness.

In the temperature and physiological monitoring subsystem 60, a plurality of distributed temperature sensors should be attached to the applicator needles or separated from them to measure the temperature distributions inside the target and surroundings. It is to be appreciated that such sensors should be of a thermometer type or optical type, which do not interfere or absorb electromagnetic energy. And the physiological monitoring may include blood pressure, heart rate, body temperature, and other general medical signs of a patient.

Preferably, the temperature sensors are distributed periodically along the inner wall of each hollow ground needle;

while at least one sensor is located at the end 63 of the outer conductor of the coaxial-cable antenna or other sensors along the antenna or separate from it. In practice, some small windows 62 made of special good heat-transfer materials are open along these hollow metal needles to make the sensors get correct temperature readings. Hence three-dimensional temperature distributions can be obtained, especially at some important points, for example, at the central point 63 (maybe also the highest temperature point) of the whole thermal field and the threshold points 62 along the boundary of the heating target. So they are effectively monitoring by a real-time means. The temperature signal is feed back from the target site to the computer 15 using some signal lines via the interface 65.

The image display subsystem 70 is used to assist precisely positioning the needles 21, 22, 23 of applicators 20 relative to the tumor location. It may employ the nuclear magnetic resonance (NMR) image techniques, ultrasound scan, or other existing computer tomographic (CT) scan methods, which have no any interference to the RF/microwave heating. The image signal is transmitted from the target site to the computer 15 using some signal lines via the interface 75.

The tunable features of the applicator need to be emphasized in a detail. A single applicator is capable of tuning to form various arrays to create different radiation patterns. Among these, the position of the coaxial cable antenna (21 plus 22) can be tunable by holding the upper portion of the slide support 27 to screw the tuner 28. The resonance length of the solid needle 22 can also be tunable by holding the lower portion of the slide support 27 to screw the tuner 29. Each of the grounded secondary needles 23 can be inserted into the different depth and along different angles and thereafter its depth can individually be adjusted by pulling/pushing the handle of the secondary needles 23. The above said three kinds of tunings make even a single applicator be flexible for different locations and different sizes of heated targets, and also create changeable thermal patterns to avoid the hot spots problem. Furthermore, more variants of either invasive or noninvasive arrays can be formed by such applicators.

It is noted that, as shown in FIG. 2, the grounded secondary needles array establishes a well-defined boundary of EM pattern 45, and also makes the EM waves continue a TEM mode propagation from the cable throughout the whole applicator. This leads to better EM mode matching and better EM uniformity, thus better energy coupling into the body. Basically, the side secondary needles greatly improve the gain directivity of the central coaxial needle antenna. Moreover, the TEM waves inside the applicator may be guided forward or back by inserting different depth of the surrounding secondary needles. Thus, the penetration depth can be adjusted, and even an asymmetrical radiation pattern can be produced for some special shaped targets. The traditional applicators radiating by TE or TM mode have no such advantages.

The size and shape of the heated target essentially determine the selection of the operating frequency, the tuning radiator length, and the spacing between the central radiator 22 and the grounded secondary needle 23. In principle, the radiator length is selected approximately to a half wavelength in tissues to improve both the selection and uniformity of heating. The array dimension of the secondary needles is set to no more than a half wavelength in order to obtain complete heating of the whole tumor volume. It is preferred that the adjacent secondary needles should no more than a quarter wavelength apart, to provide for enough shielding to the surrounded tissues. For example, a target with the overall dimension of 2.25 cm should select a frequency of 915 MHz or lower, and a 2.25 cm long radiator and around 2.25 cm grounded array should be used. In practical applications, these dimensions and frequency are chosen and adjusted according to the size and location of the target displayed by the imaging subsystem 70 and the temperature distribution inside and surrounding target tissues sensed by the monitoring subsystem 60. In addition, the amplitude and phase of each applicator is also used so as to create an optimized thermal pattern when the formed array of applicators is applied, especially by an automatic control program as described hereinafter.

Figure 3A:
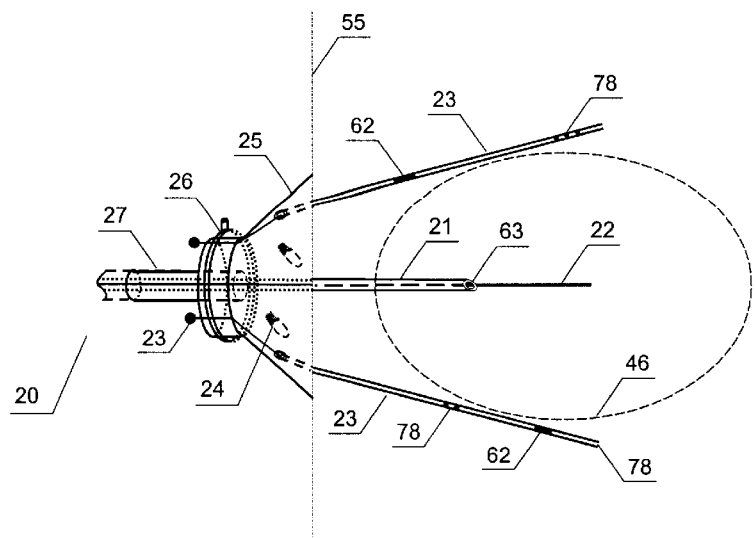
FIGS. 3(a) through 3(c) show the operation plan tuning for the different depth of therapy target and corresponding radiation patterns.
Figure 3B:
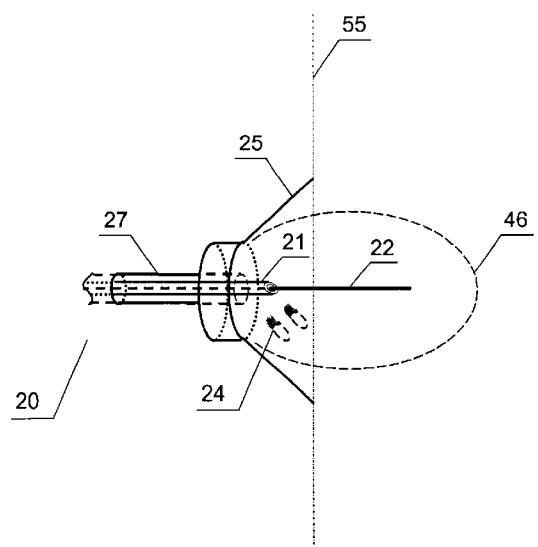
Figure 3C:
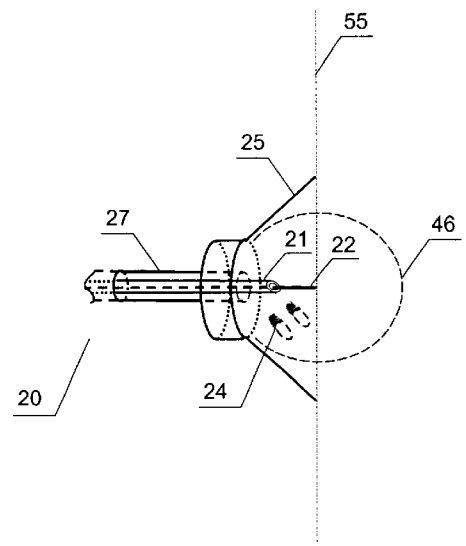

In order to properly heat different locations and sizes of target, three typical examples of insertion fashions are demonstrating in FIGS. 3(*a*), (*b*) and (*c*) respectively. Although not shown in FIG. 3, various forms of arrays, such as annular array, sub-array, three-dimensional array, and so on can be used based on the different insertion fashion.

In the case of FIG. 3(*a*), the outer needle 21, the solid needle 22, and all grounded secondary needles 23 are completely inserted into the body. In the practical operation, first adjust the solid needle 22 to be enclosed inside the hollow outer needle 21, then insert both of them together into the body either close to the target or inside the target, finally tune the solid needle 22 to be deeper for exposure from the hollow outer needle 21. Afterwards, every needle can be tunably positioned. This scheme is very suitable for heating the small deep target with a clear boundary. Since the RF/microwave energy is directly delivered to the target, no energy is lost along the bypass path. Thereby the effective penetration and efficiency of RF/microwave hyperthermia can be improved greatly. The surrounding secondary needles closely along the target boundary help bound the EM fields. And the deeper surrounding secondary needles can guide the EM waves to penetrate into the target further. Even such a single array-type applicator has a capability of RF/microwave energy focus, thus making the hyperthermia be really selected and localized. Much more improvements of selection and uniformity should be achieved by use of array of such applicators, as shown in FIG. 1. This is because adjustments of power level and relative phase from each applicator can cause a constructive interference enhancement of EM energy. Even in form of non-constructive interference of radiation, multiple applicators should also improve the heating uniformity. The tunable feature of each needle and the radiator makes the temperature peak point be possibly relocated thus improving the heating uniformity further.

For the case of FIG. 3(*b*), all grounded secondary needles 23 are removed, while only the solid needle 22 is inserted into the body. This scheme is very suitable for heating the target located at the intermediate depth. The position of the solid needle 22 can be adjusted for various targets with different locations and sizes. It has a better penetration than that of a noninvasive way because of reducing some power attenuation on the skin surface and subsurface regions. In this case, the soft horn 25 further improves the focus capability of the applicator. Similarly, a side sub-array form of such applicators can be used to improve selection and uniformity of heating, also incorporating with power level and relative phase of each applicator.

The final scheme is completely noninvasive, shown in FIG. 3(*c*), which is very suitable for both a subsurface target with single or sub-array of applicators and a deep large target with annular amplitude-phase controlled array of applicators. These two kinds of targets may need different radiation frequencies because of significantly different penetration depth required respectively. In this case also, the soft horn 25 further improves the focus capability of the applicator.

Figure 4:
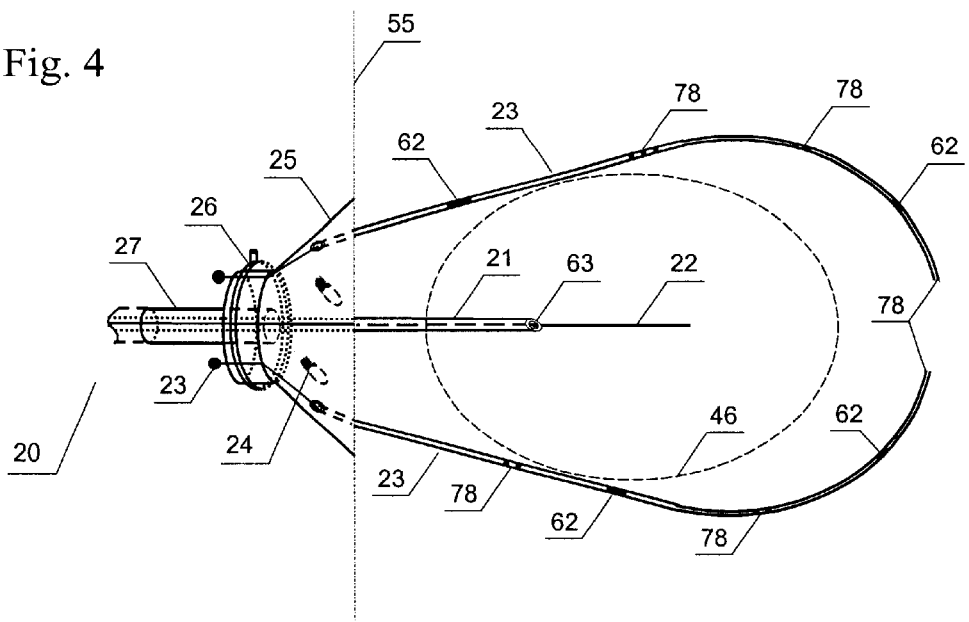
FIG. 4 shows a deflected array of hollow secondary needles to improve the focus capability of a single applicator.

In another embodiment, when a single applicator is used to treat the small deepest tumors, a further focus of RF/microwaves may need to be improved in the forward direction of the wave propagating. In this case, as in FIG. 4, the hollow grounded secondary needles 23 are deflected in a three-dimensional array. Preferably, the secondary needles are first introduced to the target site in a radially collapsed or other constrained configuration, and thereafter advanced into and surrounding the target tissues in a convergent pattern to form a uniform and symmetrical three-dimensional array. These needles may or may not meet together at the ends because they are already in a common ground. In order to achieve this kind of array, such needles can be made of conductive metals having a suitable shape memory, such as commercially available nickel-titanium alloys, spring steel alloys, and the like. The shape memory alloy is formed in a second configuration and then an external influence such as heat is applied and the alloy is shaped to a first configuration, which it retains when the influence is removed. When the influence is re-applied (i.e. the alloy is heated), it returns to its "memorized" second configuration. Thus, the needles may be inserted in the first configuration (constrained), and then, under the external influence, for example if they are heated, they change to the second configuration (converged). Any other form of shape-memory fashions and deflection methods can be used, not limited to the example given here.

At least one thermal sensor is placed at the end 63; other sensors are seeded periodically along the hollow needle through some hole windows 62. Similarly some small holes 78 and the end 63 of the central coaxial cable are open for infusion of chemical therapeutic agents. Therefore, this configuration of array needles can produce a three-dimensional infusion and subsequently to improve the infusion uniformity. And the three-dimensional temperature distributions can be monitored effectively.

Figure 5:
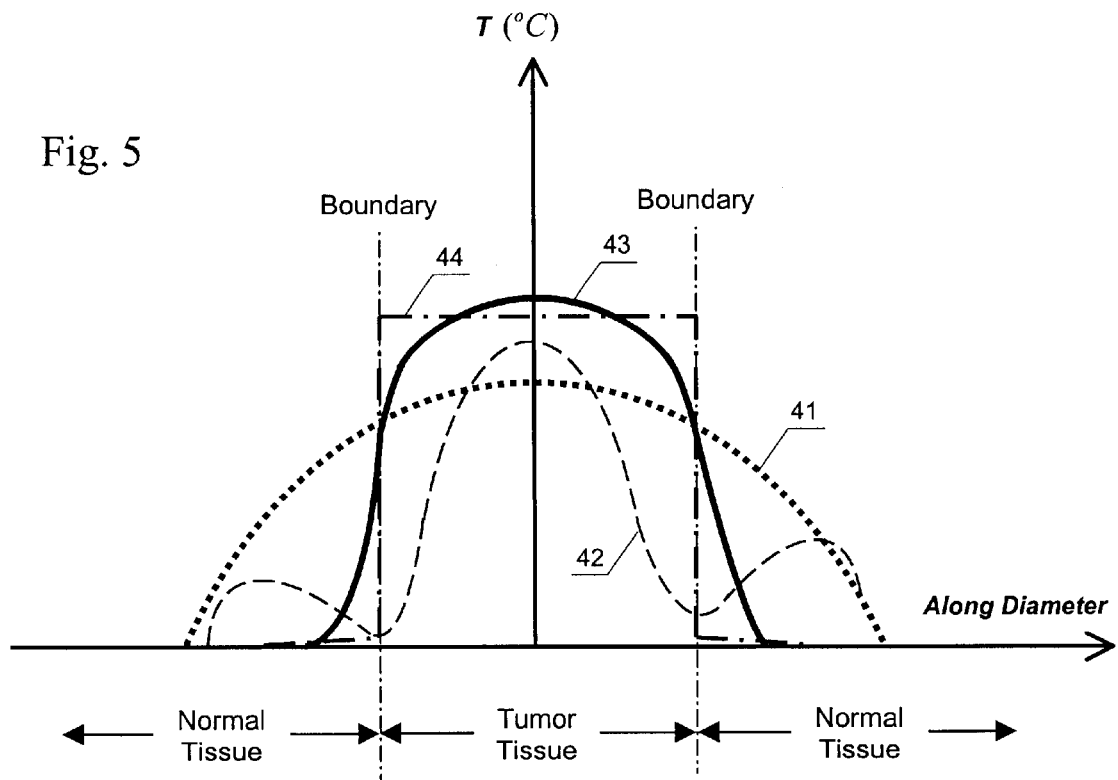
FIG. 5 shows a comparison description of trade-off among penetration, uniformity and selection of RF/microwave heating treatment.

The scheme of applying inserted small coaxial-cable antennas to deliver RF/microwave energy directly to the target tissues has overcome the difficulty of trade-off between penetration and selection. However, it is obvious that the frequency also determines the size of the radiation volume. The lower frequency is chosen, the larger size of the radiation volume must be produced, vice versa. In order to improve focus capability, the frequency should be chosen higher, but may cause not to heat effectively along the edge areas of the target tumor tissues because of the rapid power attenuation from the central of the inserted antenna. It means a good heating uniformity is not achievable. The dashed line 42 shown in FIG. 5 means that a quite large difference of temperatures obtained within the tumor volume without the surrounded ground needles. While the frequency is set too low, the RF/microwaves may propagate or scatter into the surrounded normal tissues. This means the selection of heating is not acceptable, as in the case of dotted line 41 of FIG. 5, also without any ground bounding. The trade-off between good uniformity and good selection of heating must determine an optimized frequency of exact value. In an actual application, this is very difficult job, because the human body is such a complicated EM media, and may vary with case by case. However, lowering down the operating frequency should enlarge the radiation volume thus improve the heating uniformity inside the tumor volume; while as in the present invention, introducing a set of grounded secondary needles locating along the tumor boundary to protect the surrounded normal tissues from radiation can improve the heating selection. Therefore, for a specific size of tumor volume, broader band of frequencies can be used rather than one or a few points of frequencies can be applied. And even a specific lower frequency can be suited for different size of tumors. Combing with the above coaxial-cable antenna with a flexible insertion depth, various tumor target with different size and at different depth can be treated by the invented system. And the flexible choices of the operating frequency as well as other system parameters make this system easily realize an optimization hyperthermia through an automatic control way. Thus both heating uniformity inside tumor tissues and heating selection defined well at the boundary can be achieved as an optimized heating result. It is shown in the case of solid line 43 of FIG. 5, which is approaching the ideal one, the dashed-dotted line 44.

In general, any scheme for different locations and sizes of targets must be under control of the central computer through the real time monitoring of temperature and other information to automatically tune every possible parameter, finally to achieve the optimized thermal pattern.

Figure 6:
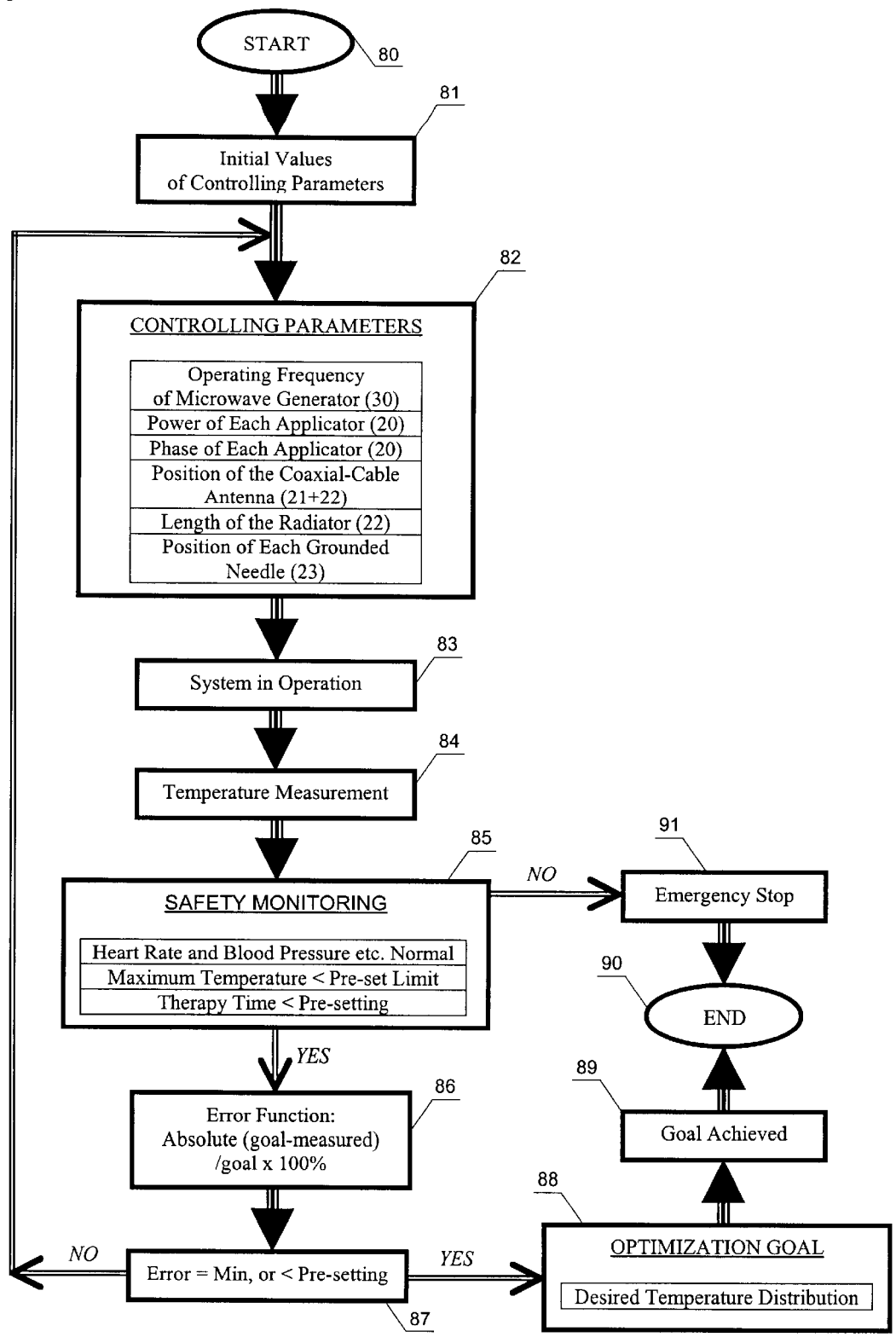
FIG. 6 is a flowchart of the automatic control diagram to achieve an optimization treatment.

The whole system can be in operation either manually or automatically. But it preferably works in an optimization mode through an automatic control flow as shown in FIG. 6. In the system, the parameters such as operating frequency of the RF/microwave generator, power of each applicator, and phase of each applicator can be set and controlled through some standard interface card, e.g., GPIB, connecting with the central computer. Other parameters such as position of the coaxial-cable antenna, length of the radiator, and position of each grounded secondary needle can be adjusted and controlled manually or preferably through a programmed motor driver to connect with the central computer. A set of initial values of these parameters 81 can be pre-set basing on the numerical predication, or animal experiment, or other clinical experience. Each set of these controlling parameters 82 produce a specific temperature distribution or thermal pattern, which is measured by some temperature sensors 62 and displayed by the temperature monitoring system 60. Varying any of the controlling parameters may create a different temperature distribution. A certain or some of sets of controlling parameters must make the system approach the desired temperature distribution, which is the pre-set optimization goal 88. It means the error function 86 approaches the minimum, or the goal has been achieved 89. Otherwise continue to do the loop until the goal is obtained, or is stopped manually or by some emergency reasons, for example, heart rate, blood pressure, or any other physiological signs monitored is abnormal, or the therapy time exceeds the pre-setting 85. The optimization goal 88 should be set reasonably, which is usually based on the numerical predication, or animal experiment, or other clinical experience. The "START" 80 and "END" 90 respectively switch on and off the program of the system.

Here gives an example of the best mode for the present apparatus to show how it works. First, should find out the target that needs to be heated according to the CT or other diagnostic means. After the location and the size of the tumor volume are determined, array form of applicators can be arranged. And each applicator with proper needles positions and insertion depths can be inserted into the patient body either in complete insertion or in partial insertion or noninvasive fashion with aid of the image display system. At this stage, some suitable infusion therapeutic agents can be introduced into the target through the central hollow needle and the surrounded hollow needles in order to improve treatment effectiveness combining with RF/microwave hyperthermia. Then fill up the soft horn with some distilled water boluses, and fix the secondary needles and connectors. After that, make sure the whole system connect correctly. Turn on the power supply of the system. And input the initial values of controlling parameters on the computer panel interface although their default values already exist. These controlling parameters may include operating frequency of RF/microwave generator, power of each applicator, phase of each applicator, position of the coaxial-cable antenna, length of the radiator, and position of each secondary needle. Their values can be pre-set basing on the numerical predication, or animal experiment, or other clinical experience. Start the automatic control program pre-installed in the computer until approaching the optimization therapy. Once the RF/microwave generator turns on, the RF/microwave power couples to each applicator through several channels at different power levels and different phases. Each coaxial-cable antenna can directly deliver the RF/microwave power into or nearby the tumor target in order to reduce the power loss along the bypass tissues. The grounded secondary needles that place along the target boundary can bound the EM waves thus not propagating or scattering into the surrounded normal tissues. Such localized RF/microwave coherent energy interacts with the dipole molecules and ions and other charged particles to evaluate the temperature locally, significantly high inside the target volume. Therefore localized RF/microwave hyperthermia with a good selection can be obtained. Furthermore, this can also enhance the chemotherapy by the pre-infused therapeutic agents. The seeded temperature sensors inside and surrounding the target feed the measured temperature information back to the central computer to realize a real-time monitoring. During the treatment, the physiological signs such as heart rate, blood pressure, and body temperature etc. of the patient arc monitored by a monitoring system. Once any of them is abnormal, or the peak temperature inside the target volume is higher than the pre-set limit, or therapy time exceeds the pre-setting, the whole system automatically goes to "Emergency Stop" status. After several tens of pre-set minutes heating treatment, a typical therapy cycle is finished.

It is concluded that all the above schemes adapting either invasive or noninvasive, either single or sub-array or array form of applicators can be integrated into a single device owing to its tunable capabilities and structure characteristics. Although the discussions so far are mainly focused on the aspect of hyperthermia applications of the invented apparatus and method, this system is straightforward to extend to the applications of the invasive and noninvasive acupuncture treatment. The only difference is that now, the target is the acupuncture point rather than a tumor. In this application, a single applicator not in array form is more appropriate due to very small target. Comparing with the hyperthermia application, higher frequency and lower power should be used in the acupuncture treatment. The RF/microwave acupuncture has the advantage of approaching much faster stimulation effect to acupuncture point over the traditional acupuncture treatment. Additional advantage of a noninvasive RF/microwave acupuncture treatment is that, unlike the traditional acupuncture treatment, the patient does not suffer pain of needle inserting. It is stated that the three schemes of FIG. 3 are still employed for the RF/microwave acupuncture applications which suit for various treating points with different depths and locations. Therefore, the presented system provides not only an effective hyperthermia approach but also a faster acupuncture treatment. It is also stated that any simplifications and modifications of this system can make it work in various modes. For example, in the simplest case, a single applicator directly connected with a single RF/microwave source with appropriate power level and frequency band can still work properly. Finally, a shielding casing can be used to enclose the whole system for a good environment protection.

Although a preferred embodiment of the invention has been described in detail, it should be understood that various substitutions, alternations, and modifications may become apparent to those skilled in the art. These changes may be made without departing from the spirit and scope of the invention as defined by the appended claims.

What is claimed is:

1. An RF/microwave hyperthermia apparatus for heating a target within a local region of body tissue, comprising:
    an RF/microwave source, generating an RF/microwave signal having a frequency and a power level, a power output at which the RF/microwave signal is output, and a ground connection;
    at least one applicator, operatively connected to the RF/microwave source, comprising:
    a coaxial needle connected to the power output of the RF/microwave source, wherein the coaxial needle comprises:
        an outer needle having a length and hollow interior having a central axis; and
        a solid needle having a length greater than length of the outer needle, located in the hollow interior of the outer needle along the central axis, such that a portion of the length of the solid needle protrudes from an end of the outer needle; and
    a plurality of secondary needles surrounding the coaxial needle connected to the ground connection of the RF/microwave source;
    such that the secondary needles guide the RF/microwave signal emitted by the coaxial needle, directing RF/microwave energy to a desired target within the body tissue.

2. The apparatus of claim 1, in which the RF/microwave source further comprises a control input.

3. The apparatus of claim 2, in which the frequency of the RF/microwave signal from the RF/microwave source may be varied by a signal applied to the control input.

4. The apparatus of claim 2, in which the power level of the RF/microwave signal from the RF/microwave source may be varied by a signal applied to the control input.

5. The apparatus of claim 1, in which there are a plurality of applicators, and further comprising a power splitter having an input connected to the power output of the RF/microwave source and a plurality of outputs connected to the coaxial needles of the plurality of applicators, such that the plurality of applicators may be arranged in the form of a radiation array such that the signals from the plurality of applicators may be converged at a desired local region of body tissue.

6. The apparatus of claim 5, further comprising an amplifier between at least one of the plurality of power outputs of the power splitter and the coaxial needles of an applicator, such that a power of the signal from at least one applicator may be changed relative to a power of the signal from at least one other applicator.

7. The apparatus of claim 5, further comprising a phase shifter between at least one of the plurality of power outputs of the power splitter and the coaxial needles of an applicator, such that a phase of the signal from at least one applicator may be changed relative to a phase of the signal from at least one other applicator.

8. The apparatus of claim 1, in which the solid needle is an acupuncture needle.

9. The apparatus of claim 1, in which the needles are made of metal having good conductivity for RF/microwave transmission.

10. The apparatus of claim 9, in which the needles are made of silver.

11. The apparatus of claim 1, in which the needles are coated with insulating material.

12. The apparatus of claim 11, in which the needles are coated with a substance selected from the group comprising polytetrafluoroethylene and diamond.

13. The apparatus of claim 1, wherein
the hollow interior of the outer needle around the solid needle is at least partially filled with an insulating material; and
the solid needle is connected to the power output of the RF/microwave source and the outer needle is connected to ground, such that the combination of the outer needle and the solid needle comprises a coaxial cable type radiator.

14. The apparatus of claim 13, in which the solid needle is movable along the axis of the hollow outer needle, such that the protruding portion of the length of the solid needle may be adjusted.

15. The apparatus of claim 13, in which the length of the protruding portion is selected to be approximately a half wavelength at the frequency of the RF/microwave signal in the body tissue.

16. The apparatus of claim 13, further comprising means for introducing therapeutic material through the hollow interior of the outer needle.

17. The apparatus of claim 13, further comprising temperature sensors located in the hollow interior of the outer needle.

18. The apparatus of claim 1, further comprising means for adjusting the length of the coaxial needle of the applicator.

19. The apparatus of claim 1, in which at least one of the secondary needles may be adjusted in position relative to the coaxial needle.

20. The apparatus of claim 1, in which an insertion depth of at least one of the secondary needles may be adjusted.

21. The apparatus of claim 1, in which an insertion angle of each secondary needle can be adjusted relative to an insertion angle of at least one other secondary needle.

22. The apparatus of claim 1, in which the plurality of secondary needles are of a number and positioned at a spacing such that the spacing between two adjacent secondary needles is not more than a quarter of a wavelength at the frequency of the RF/microwave signal in the body tissue.

23. The apparatus of claim 1, in which at least one of the secondary needles has a hollow interior.

24. The apparatus of claim 23, further comprising means for introducing therapeutic material through the hollow interior of the secondary needle.

25. The apparatus of claim 23, further comprising temperature sensors located in the hollow interior of the secondary needle.

26. The apparatus of claim 1, in which at least one of the secondary needles is made of a material having a shape memory.

27. The apparatus of claim 1, further comprising a shielding horn connected to ground, and at least partially surrounding the coaxial needle and secondary needles.

28. The apparatus of claim 27, in which the shielding horn is made of flexible material.

29. The apparatus of claim 28, in which the flexible material is RF/microwave-shielding cloth.

30. The apparatus of claim 27, further comprising at least one deionized water bolus located between the applicator and the body tissue.

31. A method for heating targets within a body with RF/microwave radiation using an RF/microwave source, generating an RF/microwave signal having a frequency and a power level, a power output at which the RF/microwave signal is output, and a ground connection; at least one applicator, operatively connected to the RF/microwave source, the applicator comprising: a coaxial needle comprising a hollow outer needle connected to the ground connection of the RF/microwave source and a solid needle connected to the power output of the RF/microwave source adjustably located within the hollow outer needle, such that a portion of the length of the solid needle protrudes from an end of the outer needle; and a plurality of secondary needles surrounding the coaxial needle, connected to the ground connection of the RF/microwave source; the method comprising the steps of:
a) contacting the body with the coaxial needle in proximity to the target or inside the target;
b) adjusting the portion of the length of the solid needle which protrudes from the end of the outer needle, the exposed end forming a radiation portion;
c) adjusting the position of the secondary needles;
d) applying the RF/microwave energy from the RF/microwave source.

32. The method of claim 31, in which there are a plurality of applicators, and steps (a) through (d) are repeated for each applicator.

33. The method of claim 32, in which at least one of the frequency, phase or power of the RF/microwave energy applied to at least one of the applicators is adjustable, and the method further comprises the step, after step (d), of adjusting at least one of the frequency, phase or power of the RF/microwave energy applied to at least one applicator.

34. The method of claim 33, in which the adjustment step is performed by a programmed computer.

35. The method of claim 32, further comprising the step of aligning the applicators in the form of a radiation array such that the RF/microwave signal from the plurality of applicators converges on the target.

36. The method of claim 31, in which step c) comprises the steps of:
i) introducing the secondary needles to the target site in a constrained configuration, and
ii) advancing the secondary needles into and surrounding the target tissues in a convergent pattern to form a uniform and symmetrical three-dimensional array.

37. The method of claim 36, in which the constrained configuration is radially collapsed.

38. The method of claim 36, in which the secondary needles are made of a material having a shape-memory, such that the needles have a first configuration and a second configuration, and the material may be induced to change from the first configuration to the second configuration by application of an external influence, and the needles are introduced in step (c)(i) in the first configuration, the method further comprising the step, between steps (c)(i) and (c)(ii), of applying the external influence to the secondary needles such that they transition from the first configuration to the second configuration.

39. The method of claim 38, in which the step of applying the external influence comprises heating the secondary needles.

40. The method of claim 31, in which step (c) comprises inserting the secondary needles into the body tissue along a boundary of the target.

41. The method of claim 31, in which the coaxial needle is at least partially hollow, and the method further comprises the step of introducing therapeutic material into the body tissue through the coaxial needle.

42. The method of claim 31, in which at least one secondary needle is at least partially hollow, and the method further comprises the step of introducing therapeutic material into the body tissue through the hollow secondary needle.

43. The method of claim 31, in which at least one of the frequency or power of the RF/microwave signal is adjustable, and the method further comprises the step, after step (d), of adjusting at least one of the frequency or power of the RF/microwave signal being applied to the applicator.

44. The method of claim 43, in which the step is performed by a programmed computer.

45. The method of claim 31, in which at least the coaxial needle of an applicator contacts with an acupuncture point of the body for noninvasive acupuncture treatment.

46. The method of claim 31, in which the body is contacted by the coaxial needle by inserting the coaxial needle into the body tissue.

47. The method of claim 31, in which at least the coaxial needle of an applicator is inserted into an acupuncture point of the body for invasive acupuncture treatment.

* * * * *